United States Patent [19]

Kvalo et al.

[11] Patent Number: 4,955,385
[45] Date of Patent: Sep. 11, 1990

[54] ULTRASOUND TARGETING SYSTEM FOR SHOCKWAVE LITHOTRIPSY

[75] Inventors: Michael L. Kvalo, Oxford, Ga.; Culley C. Carson, Durham, N.C.

[73] Assignee: C. R. Bard, Inc., Murray Hill, N.J.

[21] Appl. No.: 306,549

[22] Filed: Feb. 6, 1989

[51] Int. Cl.$^5$ .......................................... A61B 17/22
[52] U.S. Cl. ............................. 128/660.03; 128/24 A
[58] Field of Search ................ 128/328, 24 A, 662.03, 128/661.07, 660.03; 606/127–128

[56] References Cited

U.S. PATENT DOCUMENTS

| | | |
|---|---|---|
| 3,779,234 | 12/1973 | Eggleton et al. . |
| 3,938,502 | 2/1976 | Bom . |
| 4,024,873 | 5/1977 | Antoshkiw et al. . |
| B1 4,024,873 | 9/1984 | Antoshkiw et al. . |
| 4,349,033 | 9/1982 | Eden . |
| 4,509,523 | 4/1985 | Pevsner . |
| 4,582,067 | 4/1986 | Silverstein et al. ............ 128/662.06 |
| 4,589,415 | 5/1986 | Haaga ................................ 128/328 |
| 4,689,986 | 9/1987 | Larson et al. .................. 128/660.03 |
| 4,696,297 | 9/1987 | Pleines et al. . |
| 4,723,556 | 2/1988 | Sussman . |
| 4,741,008 | 4/1988 | Franke . |

FOREIGN PATENT DOCUMENTS

| | | |
|---|---|---|
| 0268019 | 5/1988 | European Pat. Off. ............ 128/328 |
| 2509584 | 7/1976 | Fed. Rep. of Germany ..................... 128/661.08 |
| 2929799 | 1/1981 | Fed. Rep. of Germany ..................... 128/660.08 |
| 3506249 | 8/1986 | Fed. Rep. of Germany ...... 128/328 |
| 2106758 | 5/1987 | Japan ................................. 128/328 |

Primary Examiner—William E. Kamm
Assistant Examiner—John D. Zele
Attorney, Agent, or Firm—Dennison, Meserole, Pollack & Scheiner

[57] ABSTRACT

A procedure for targeting body cavity stones for shockwave treatment including positioning a target-defining catheter mounted balloon adjacent a stone, inflating the balloon with air, focusing a shockwave generator by ultrasound on the target balloon and area immediately adjacent thereto, and deflating the target balloon.

14 Claims, 1 Drawing Sheet

ULTRASOUND TARGETING SYSTEM FOR SHOCKWAVE LITHOTRIPSY

BACKGROUND OF THE INVENTION

Ultrasound guided shockwave lithotripsy, commonly known as ESWL or extracorporeal shockwave lithotripsy, refers to a system for treating stones or calculi, normally by disintegration for ultimate removal or discharge from the body.

It is particularly desirable to properly focus the shock waves on the stone to avoid damage to healthy tissue about the stone. However, ureteral stones are very difficult, if not impossible, to visualize with ultrasound, and thus accurate focusing of the equipment has been a problem.

One known procedure, in lithotripsy systems, for location of calculi to be disintegrated involves the use of x-ray means and is referred to in U.S. Pat. No. 4,741,008, issued to Kurt Franke on Apr. 26, 1988. This x-ray means normally comprises rather elaborate equipment particularly adpated for use as an adjunct of the lithotripsy equipment to provide a visual representation of a calculi.

BACKGROUND OF THE INVENTION

The present invention proposes an alternate and substantially improved system for properly focusing or directing the shockwaves when treating ureteral stones with ultrasound guided shockwave lithotripsy. Basically, a target highly visible to ultrasound is positioned immediately adjacent the stone within the ureter with the shockwave focused on the target or in the immediate vicinity thereof. After focusing, the target can be withdrawn.

More specifically, the present invention proposes a catheter target comprising an elongate catheter with an inflatable balloon mounted on the leading end thereof. The balloon defines the actual stone engaging target.

The target to be effective must have good ultrasound visualization, and as such, must comprise a material or be of a nature to provide a significantly different acoustical impedance from the surrounding body tissue. This requirement is uniquely met by air which, when used as the inflation medium for the catheter balloon, provides an inexpensive and highly effective ultrasound target.

In performing a lithotripsy procedure utilizing a target catheter, the target catheter is placed through a cystoscope under fluoroscopy up to and immediately adjacent the distal side of the stone. The cystoscope is then removed and the patient positioned for the shockwave procedure. When ultrasonically focusing the shockwave, the balloon is inflated with air to provide the desired high visualization. As the physician is aware that the stone is just to the proximal side of the balloon, the equipment can now be accurately directed after which the balloon, as desired, may be deflated. The use of an inflatable balloon as the target, particularly with the inflation medium being air, enables a selective deflation and re-inflation of the target balloon should such be necessary to verify location of the target and proximal stone.

It is particularly preferred that the balloon be expandable beyond the leading end of the catheter with no portion of the catheter going through the balloon itself as in the more conventional balloon catheter. This is preferred in that there will be no internal echoes from the balloon, but rather, only a small, cystic-appearing structure on the ultrasound.

Catheters with end-positioned balloons are known and have been used for a variety of purposes. For example, before ESWL procedures, a similar catheter with an inflatable balloon end had been used to propel stones from the ureter back into the kidney. However, with the advent of ESWL, the use of this propelling procedure diminished. There was no suggestion of utilizing such balloon catheters as targets in an ultrasound guided shockwave lithotripsy procedure.

Additional objects and features of the invention will become apparent from the details of the invention as more fully hereinafter described and claimed.

DESCRIPTION OF PREFERRED EMBODIMENT

Figure 1:
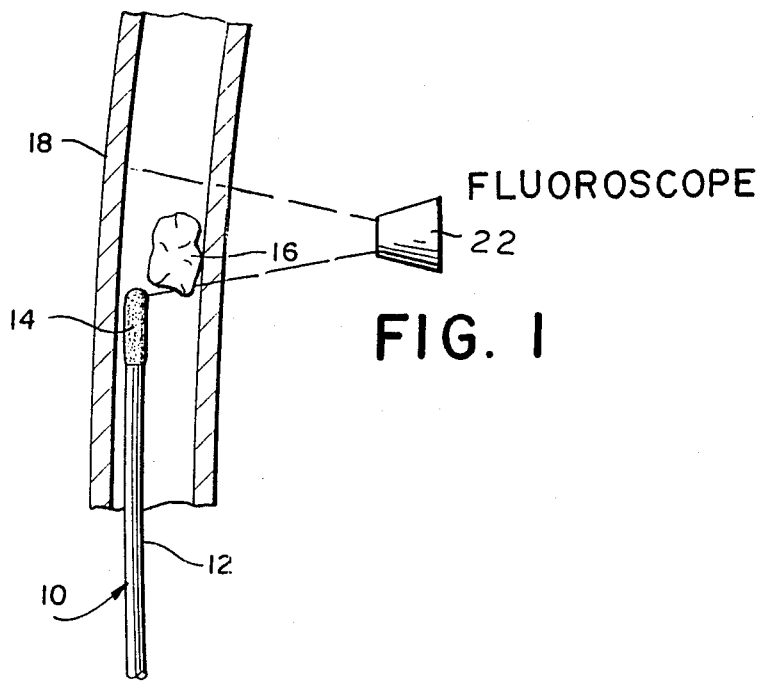
FIG. 1 is a schematic view illustrating introduction of the target catheter into the ureter toward an internal stone or calculi.

The target catheter 10 includes a conventional catheter 12, which may be on the order of 5F (French) by 69 centimeters, with an inflatable latex balloon 14 mounted on the leading end of the catheter. The balloon 14 is to be inflatable to about 18F. The letter F (French) is a conventional size designation with 3F equaling approximately one millimeter.

The drawing schematically illustrate the insertion and location of the target catheter in treating a ureteral stone 16 located within the ureter 18. The primary purpose of the invention is to provide a system whereby a non-invasive lithotriptor or shockwave generator 20 can be accurately focused on the stone or calculi 16 for disintegration of the stone with little or no damage to the healthy surrounding tissue.

The procedure initially involves an insertion of the target catheter 10 to position the target-defining balloon 14. The target catheter will normally be placed through a cystoscope under fluoroscopy as schematically suggested at 22 in FIG. 1. As such, the catheter body is preferably radiopaque for good visibility under fluoroscopy.

The target balloon 18 is preferably placed immediately against the distal side of the stone, after which the cystoscope is removed.

The patient is then taken for ESWL, or extracorporeal shockwave lithotripsy. As an initial step, the balloon is inflated with air. Air is the preferred inflation medium in that the defined air cavity provides a significantly different acoustical impedance from body tissue. This in turn results in good ultrasound visualization. Inflation of the balloon can be conventionally effected utilizing a syringe and approximately ½ cc. of air.

Figure 2:
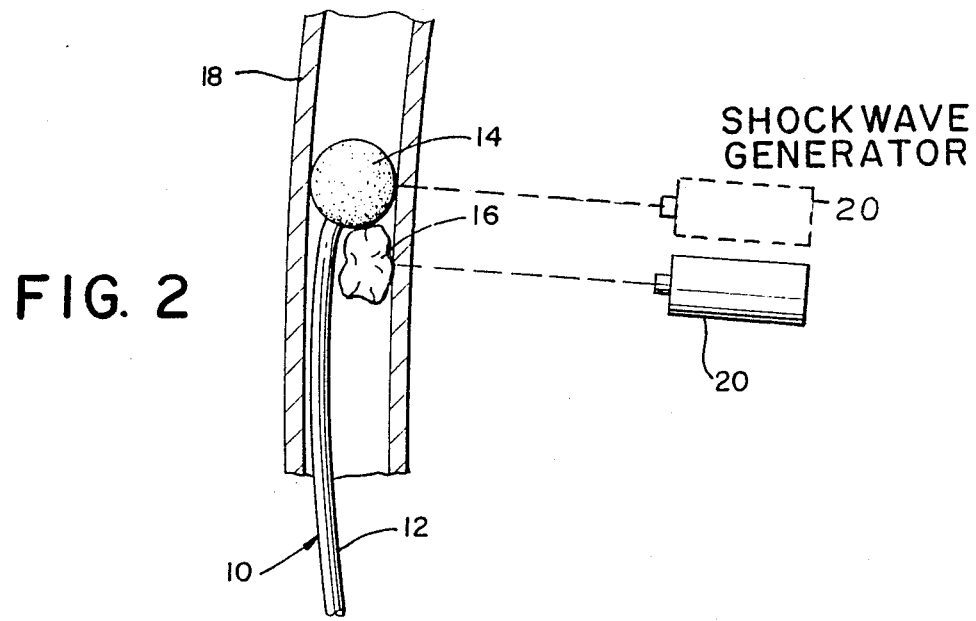
FIG. 2 is a schematic view illustrating the target-defining balloon inflated immediately distal of the stone.

By a positioning of the target balloon just to the distal side of the stone, the physician knows the stone is just proximal to the balloon. As such, the lithotriptor or shock wave generator can be accurately focused on the stone, as suggested in FIG. 2. Subsequent to a focusing of the shock wave generator, the balloon can be deflated, if desired, to avoid any potential interference with stone disintegration.

If considered necessary to verify location of the target balloon and stone, the target balloon, through the catheter, can be easily alternatively deflated and inflated in an obvious and simple manner. The target catheter may, of course, be removed as desired either upon a targeting of the shockwaves or a completion of the entire procedure.

As previously noted, the target balloon is provided on the extreme leading end of the catheter to avoid the catheter going through the center portion of the balloon. Thus, there will be no internal echoes from the balloon, but rather, only a small, cystic appearing structure on ultrasound which forms a readily defined target, particularly when the fluid inflation medium is air.

Variations in means and procedures may be suggested to those skilled in the art. It is intended that the scope of the invention be such as to encompass all such variations as may be within the scope of the invention as herein presented and claimed.

We claim:

1. A method of targeting a stone within a body cavity by ultrasound for treatment of the stone by shockwave lithotripsy comprising the steps of; providing a catheter including a leading end with an inflatable balloon mounted thereat, introducing the leading end of the catheter and the balloon into the body cavity, positioning the balloon immediately adjacent the stone, inflating the balloon to define a target, ultrasonically locating the target and focusing a shockwave lithotriptor relative to the located target and on the stone to target the stone for emitted shockwaves, thereby enabling treatment of the stone.

2. The method of claim 1 wherein the step of providing a catheter with a balloon further comprises extending said balloon forward of the leading end of the catheter.

3. The method of claim 2 wherein the inflating step further comprises inflating said balloon with a fluid medium which defines a target highly visible with ultrasound.

4. The method of claim 3 wherein the inflating step further comprises inflating the balloon with air.

5. The method of claim 4 wherein the method further comprises the step of deflating said balloon after focusing said shockwave lithotriptor.

6. The method of claim 5 wherein said stone has a distal side and said balloon has a proximal side, and wherein the step of positioning said balloon further comprises positioning said balloon on the distal side of the stone and wherein the step of focusing said shockwave lithotriptor further comprises focusing said lithotriptor adjacent the proximal side of the balloon.

7. The method of claim 6 wherein said catheter is radiopaque and the step of positioning the balloon further comprises guiding the balloon to position by fluoroscopy.

8. The method of claim 6 wherein the method further comprises the step of selectively deflating and inflating the balloon to verify its location by ultrasound.

9. The method of claim 1 wherein the inflating step further comprises inflating said balloon with a fluid medium which defines a target highly visible with ultrasound.

10. The method of claim 9 wherein the step of positioning said balloon further comprises positioning the balloon to a predetermined side of the stone whereby said stone is in a known position relative to the balloon.

11. A method of targeting a ureteral stone within the ureter by ultrasound for treatment of the stone by shockwave lithotripsy comprising the steps of; introducing an ultrasound target within the ureter, positioning the target immediately adjacent the stone, locating the target using ultrasound and focusing a non-invasive shockwave generator relative to the target and on the stone, whereby a focused shockwave can be directed to the stone for treatment thereof.

12. The method of claim 11 wherein the step of positioning said target further comprises positioning said target to a predetermined side of the stone whereby said stone is in a known position relative to the target.

13. A method of targeting a stone within a body cavity by ultrasound for treatment of the stone by shockwave lithotripsy comprising the steps of; introducing an ultrasound target within the body cavity, positioning the target immediately adjacent the stone, locating the target using ultrasound and focusing a shockwave generator relative to the target, whereby a focused shockwave is directed to the stone, said stone having a distal side and said target having a proximal side; and wherein the step of positioning said target further comprises positioning said target on the distal side of the stone, whereby said stone is in a known position relative to the target, said step of focusing the shockwave generator further comprises focusing to the proximal side of the target.

14. A mehtod of targeting a stone within a body cavity by ultrasound for treatment of the stone by shockwave lithotripsy comprising the steps of; providing a catheter including a leading end with an ultrasound target thereat, introducing the leading end of the catheter and the target into the body cavity, positioning the target immediately adjacent the stone, ultrasonically locating the target and focusing a non-invasive shockwave lithotriptor relative to the located target and on the stone to target the stone for emitted shockwaves, thereby enabling treatment of the stone.

* * * * *